United States Patent [19]

Schneider et al.

[11] Patent Number: 4,529,730
[45] Date of Patent: Jul. 16, 1985

[54] PIPERIDINE DERIVATIVES, THEIR PREPARATION AND PHARMACEUTICAL COMPOSITIONS CONTAINING THEM

[75] Inventors: Roland Schneider, Conflans St Honorine; Christian Warolin, Paris; Dennis Bigg, Jouy en Josas, all of France

[73] Assignee: Synthelabo, Paris, France

[21] Appl. No.: 504,113

[22] Filed: Jun. 14, 1983

Related U.S. Application Data

[63] Continuation of Ser. No. 313,573, Oct. 21, 1981, abandoned.

[51] Int. Cl.$^3$ .................. A61K 31/445; C07D 211/46
[52] U.S. Cl. ..................... 514/319; 546/205; 546/216; 546/221; 546/197; 514/327; 514/321
[58] Field of Search .............. 546/216, 205, 221; 424/267

[56] References Cited

U.S. PATENT DOCUMENTS

| 2,716,122 | 8/1955 | Levy et al. | 546/216 |
| 2,751,388 | 6/1956 | Levy | 546/216 |
| 2,831,862 | 4/1958 | Biel | 546/216 |
| 2,974,146 | 3/1961 | Biel | 546/216 |
| 3,260,723 | 7/1966 | L'Italien et al. | 546/216 |
| 3,542,794 | 11/1970 | Helsley | 546/216 |
| 3,743,645 | 7/1973 | Helsley | 546/216 |

FOREIGN PATENT DOCUMENTS 15817  9/1980  European Pat. Off. .

Primary Examiner—Norma S. Milestone
Attorney, Agent, or Firm—Wegner & Bretschneider

[57] ABSTRACT

A piperidine derivative of the formula:

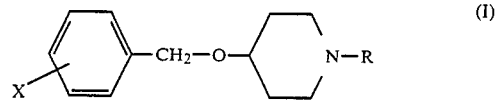

(I)

wherein R represents a hydrogen atom, a $(C_{1-4})$alkyl, hydroxy$(C_{1-4})$alkyl, $(C_{1-4})$alkoxycarbonyl or benzyl radical, or a benzyl radical carrying a substituent selected from halogen atoms and $(C_{1-4})$alkoxy radicals, or the phenethyl or 3-phenylpropyl radical, and X represents one or more hydrogen or halogen atoms or $(C_{1-4})$alkyl, $(C_{1-4})$alkoxy, trifluoromethyl or methylenedioxy radicals, or alternatively X forms with the phenyl nucleus a naphthyl radical, with the proviso that when R represents a hydrogen atom X is other than a hydrogen atom, are new compounds useful in therapy and, more particularly, as antidepressants.

3 Claims, No Drawings

PIPERIDINE DERIVATIVES, THEIR PREPARATION AND PHARMACEUTICAL COMPOSITIONS CONTAINING THEM

This application is a continuation of application Ser. No. 313,573, filed Oct. 21, 1981, now abandoned.

DESCRIPTION

The present invention relates to new therapeutically useful piperidine derivatives, to a process for their preparation, pharmaceutical compositions containing them and their use in therapy.

The piperidine derivatives of the present invention are those compounds of the general formula:

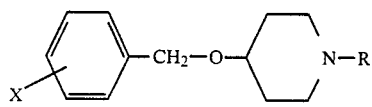

(I)

wherein R represents a hydrogen atom, or a $(C_{1-4})$alkyl, hydroxy$(C_{1-4})$alkyl, or $(C_{1-4})$alkoxycarbonyl radical, or a benzyl radical optionally carrying a substituent selected from halogen atoms and $(C_{1-4})$alkoxy radicals, or the phenethyl radical, or the 3-phenylpropyl radical, and X represents one or more hydrogen or halogen atoms or $(C_{1-4})$alkyl, $(C_{1-4})$alkoxy, trifluoromethyl or methylenedioxy radicals, or alternatively X forms with the phenyl nucleus a naphthyl radical, with the proviso that when R represents a hydrogen atom X is other than a hydrogen atom, and pharmaceutically acceptable acid addition salts thereof.

The piperidine derivatives of general formula (I) are therapeutically useful in that they possess antidepressive activity.

Preferred compounds of the invention are those of general formula (I) wherein X represents one or more chlorine atoms, or forms with the phenyl nucleus a naphthyl radical, or represents three methoxy radicals.

Of that class, those piperidine derivatives wherein R represents a hydrogen atom are particularly preferred.

According to a feature of the present invention, the piperidine derivatives of general formula (I) are prepared by the process which comprises the reaction of a compound of the general formula:

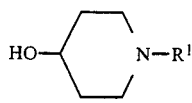

(II)

(wherein $R^1$ represents a radical within the definition of symbol R, or a nitrogen-protecting radical such as an optionally substituted benzoyl radical, e.g. 4-nitrobenzoyl, or an optionally substituted benzyl or alkyl radical) with a compound of the general formula:

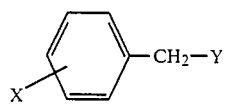

(III)

(wherein Y represents a reactive radical such as a chlorine or bromine atom, and X is as hereinbefore defined) and, when $R^1$ in the product obtained of the general formula:

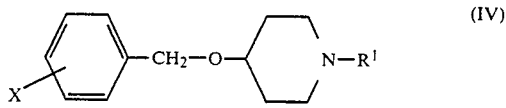

(IV)

is other than a radical R as hereinbefore defined, removing the nitrogen-protecting radical to yield a compound of general formula (I) wherein R represents a hydrogen atom, or reducing by methods known per se an optionally substituted benzoyl radical $R^1$ in the compound of general formula (IV) to a corresponding benzyl radical, as is within the definition of symbol R.

According to a further feature of the invention, a piperidine derivative of the general formula:

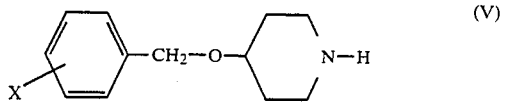

(V)

(wherein X is as hereinbefore defined) so obtained by the aforedescribed process is converted to another compound of general formula (I) by reaction with a compound of the general formula:

$Z-R^2$ (VI)

wherein Z represents a reactive atom or group, e.g. a halogen atom, and $R^2$ represents a $(C_{1-4})$alkyl, hydroxy$(C_{1-4})$alkyl or $(C_{1-4})$alkoxycarbonyl radical, or a benzyl radical optionally carrying a substituent selected from halogen atoms and $(C_{1-4})$alkoxy radicals, or the phenethyl radical or the 3-phenylpropyl radical.

Pharmaceutically acceptable acid addition salts of the piperidine derivatives of general formula (I), e.g. mandelates, fumarates, citrates and hydrochlorides, may be obtained by methods known per se, for example by treatment of the piperidine base with the appropriate acid in a solvent medium, e.g. an ether or an alkanol.

By the term 'methods known per se' as used in this specification is meant methods heretofore used or described in the literature.

The following Examples illustrate the preparation of piperidine derivatives of the present invention and acid addition salts thereof by the hereinbefore described process. The analyses and the IR and NMR spectra confirm the structure of the compounds.

EXAMPLE 1

4-(4-Fluorobenzyloxy)-piperidine and its mandelate

1(1)

1-(4-Nitrobenzoyl)-4-(4-fluorobenzyloxy)-piperidine

A mixture of 1.6 g of a 50% aqueous sodium hydroxide solution, 10 ml of methylene chloride, 2 g (0.008 mol) of 1-(4-nitrobenzoyl)-4-hydroxypiperidine, 2.32 g (0.012 mol) of 4-fluorobenzyl bromide and 0.15 g $(4 \times 10^{-4}$ mol) of tetrabutylammonium iodide is stirred for 5 hours at 50° C. After dilution of the reaction medium with 20 ml of water and 30 ml of methylene chloride, the organic phase is decanted, washed with water until the washings are neutral, dried (MgSO$_4$) and evaporated in vacuo. The residual oil obtained crystallises on stirring in diethyl ether. This yields 2.23 g of a product which is purified by dissolving it in 11 ml of dimethylformamide (DMF) and reprecipitating it by the dropwise addition of 11 ml of water, whilst stirring. After washing with water and drying in vacuo, 1-(4-nitrobenzoyl)-4-(4-fluorobenzyloxy)-piperidine, m.p. 120° C., is obtained.

1(2) 4-(4-Fluorobenzyloxy)-piperidine (mandelate)

A mixture of 11.48 g (0.032 mol) of the product obtained under 1(1), 192 ml of 96° ethanol and 48 ml of 10M aqueous potassium hydroxide solution is stirred under nitrogen and heated for 4 hours at 50° C. The alcohol is driven off in vacuo and the residue is taken up in 200 ml of water, 72 g of sodium chloride and 200 ml of diethyl ether. After filtration, the aqueous phase is extracted twice with 200 ml of diethyl ether and the total organic phase is dried (MgSO$_4$) and evaporated in vacuo.

This yields an oil which is converted to the d,l-mandelate by dissolving it in 100 ml of diethyl ether and adding 4.57 g (0.03 mol) of d,l-mandelic acid. The salt obtained is filtered off and recrystallised from isopropanol. Its melting point is 146° C.

EXAMPLE 2

4-(3,4,5-Trimethoxybenzyloxy)-piperidine and its mandelate

2(1) 1-(4-Nitrobenzoyl)-4-(3,4,5-trimethoxybenzyloxy)-piperidine

A mixture of 0.8 g of 50% aqueous sodium hydroxide solution, 5 ml of methylene chloride, 1 g (0.004 mol) of 1-(4-nitrobenzoyl)-4-hydroxypiperidine, 1.30 g (0.006 mol) of 3,4,5-trimethoxybenzyl chloride and 0.08 g (2×10$^{-4}$ mol) of tetrabutylammonium iodide is stirred for 5 hours at 50° C. After dilution with 10 ml of water and 15 ml of methylene chloride, the organic phase is decanted, washed with water until the washings are neutral, dried (MgSO$_4$) and evaporated in vacuo. The residual oil obtained crystallises on stirring in diethyl ether. This yields 1.36 g (79%) of a product which is purified by dissolving it in 7 ml of DMF and slowly reprecipitating it with 7 ml of water. After washing with water and drying in vacuo, 1-(4-nitrobenzoyl)-4-(3,4,5-trimethoxybenzyloxy)-piperidine, m.p. 124° C., is obtained.

2(2) 4-(3,4,5-Trimethoxybenzyloxy)-piperidine (mandelate)

A mixture of 12 g (0.028 mol) of the product obtained under 2(1), 168 ml of 96° ethanol and 48 ml of 10M aqueous potassium hydroxide solution is stirred under nitrogen and heated for 4 hours at 50° C. The alcohol is driven off in vacuo and the residue is taken up in 70 ml of water, 25.2 g of sodium chloride and 70 ml of chloroform. After filtration, the aqueous phase is extracted twice with 70 ml of chloroform and the total organic phase is dried (MgSO$_4$) and evaporated in vacuo. This yields a pasty solid which is converted to the d,l-mandelate by dissolving it in 120 ml of methanol, adding 4.26 g (0.028 mol) of d,l-mandelic acid and filtering the medium after it has been stirred overnight at ambient temperature. The precipitate obtained is recrystallised from methanol. The product crystallises with half a molecule of water. Its melting point is 114° C.

EXAMPLE 3

1-Ethoxycarbonyl-4-benzyloxypiperidine

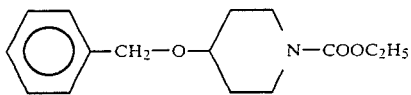

3,4 g (0.033 mol) of ethyl chloroformate are added dropwise to a stirred mixture of 6.83 g (0.03 mol) of 4-benzyloxypiperidine hydrochloride, 7.74 g (0.056 mol) of dry K$_2$CO$_3$, 26 ml of water and 26 ml of chloroform. After stirring for 1 hour, the organic phase is decanted after dilution with 54 ml of chloroform, and washed 3 times with 20 ml of water and dried (MgSO$_4$). Evaporation of the solvent in vacuo gives a liquid, which is distilled in vacuo.

Boiling point (0.4 mm Hg): 149°–151° C.; n$_D^{21}$=1.5178.

EXAMPLE 4

1-Methyl-4-(4-chlorobenzyloxy)-piperidine and its hydrochloride

In a 500 ml three-necked round-bottomed flask placed under an argon atmosphere, 4.4 g (0.1 mol) of a 55% suspension of sodium hydride in oil are washed 3 times with petroleum ether. 10.1 g (0.1 mol) of 1-methyl-4-hydroxypiperidine, dissolved in 100 ml of DMF, are then added. The mixture is stirred for 1 hour at ambient temperature and then cooled with a bath of iced water, and 19.3 g (0.12 mol) of p-chlorobenzyl chloride, dissolved in 50 ml of DMF, are added. Once the introduction has ended, the mixture is stirred for 4 hours at ambient temperature and left to stand overnight. The reaction medium is poured into iced water and extracted 3 times with diethyl ether. The organic phase is washed once with water and then extracted with dilute HCl (1–2N). The aqueous phase is then rendered alkaline with NaOH. It is extracted with diethyl ether and the ether extract is then washed 4 times with water. It is dried over magnesium sulphate, filtered and concentrated. The oil obtained is distilled twice and the fraction passing over at 94°–98° C./0.04 mm Hg is collected. This yields an oil, which is taken up in diethyl ether, and the hydrochloride is precipitated by adding hydrogen chloride. The hydrochloride is filtered off and rinsed with diethyl ether. It is taken up in the minimum amount of hot isopropanol, 5 times the volume of ethyl acetate is then added and the compound is left to recrystallise. The hydrochloride melts at 149°–151° C.

EXAMPLE 5

1-Benzyl-4-(3,4,5-trimethoxybenzyloxy)-piperidine and its fumarate

In a 250 ml three-necked round-bottomed flask placed under a nitrogen atmosphere, 2.2 g (0.05 mol) of a 55% suspension of sodium hydride in oil are washed 3 times with petroleum ether. 9.6 g (0.05 mol) of 1-benzyl-4-hydroxypiperidine, dissolved in 30 ml of DMF, are then introduced. Once the addition has ended, the mixture is stirred for 1 hour at ambient temperature. 13 g (0.06 mol) of 3,4,5-trimethoxybenzyl chloride in 30 ml of DMF are then added, whilst cooling with a bath of iced water. The mixture is stirred for 5 hours at ambient temperature and then left to stand overnight. The reaction medium is poured into iced water and then extracted with diethyl ether. The product is then extracted with dilute HCl. The aqueous phase is rendered alkaline with NaOH and then extracted with diethyl ether, and the ether extract is washed with water, dried over MgSO$_4$, filtered and concentrated. The oil obtained is taken up in hot pentane. The product crystallises. It is filtered off and recrystallised from isopropanol. This yields the base, which is dissolved in 70 ml of ethanol, and a filtered solution of 2.9 g (0.025 mol) of fumaric acid in 140 ml of ethanol is added. The fumarate salt formed is filtered off and dried. Its melting point is 160°–161° C.

EXAMPLE 6

1-(4-Chlorobenzyl)-4-(3,4,5-trimethoxybenzyloxy)-piperidine and its fumarate

6(1) 1-(4-Chlorobenzoyl)-4-hydroxypiperidine 30 g (0.296 mol) of 4-hydroxypiperidine, 260 ml of CHCl$_3$, 57.3 g (0.414 mol) of K$_2$CO$_3$ and 260 ml of water are placed in a one liter Erlenmeyer flask, 51.8 g (0.296 mol) of p-chlorobenzoyl chloride, dissolved in 50 ml of CHCl$_3$, are added in the course of 15 minutes, whilst cooling with a bath of iced water. The mixture is stirred overnight at ambient temperature. The organic phase is decanted, the aqueous phase is extracted with CHCl$_3$ and the CHCl$_3$ extract is washed with water until the pH is 6–7. It is dried over MgSO$_4$, filtered and concentrated. The product is recrystallised from ethyl acetate.

6(2) 1-(4-Chlorobenzoyl)-4-(3,4,5-trimethoxybenzyloxy)-piperidine

In a three-necked round-bottomed flask under a nitrogen atmosphere, 0.96 g (0.022 mol) of a 55% suspension of sodium hydride in oil is washed 3 times with petroleum ether. 4.8 g (0.02 mol) of 1-(4-chlorobenzoyl)-4-hydroxypiperidine obtained as described in 6(1), dissolved in 50 ml of DMF, are then added. After the addition has ended, the mixture is stirred for 1 hour at ambient temperature. It is then cooled with a bath of iced water, and 5.4 g (0.025 mol) of 3,4,5-trimethoxybenzyl chloride, dissolved in 10 ml of DMF, are added. The mixture is stirred for 3 hours at ambient temperature and then left to stand overnight. It is poured into iced water and extracted with ethyl acetate. The ethyl acetate extract is washed with water, dried over MgSO$_4$, filtered and concentrated. The oil obtained is taken up in diethyl ether and the solution is then filtered. The filtrate is concentrated and passed through an alumina column (eluant: CHCl$_3$). The product does not crystallise and is used as such in the following step.

6(3) 1-(4-Chlorobenzyl)-4-(3,4,5-trimethoxybenzyloxy)-piperidine and its fumarate In a round-bottomed flask under a nitrogen atmosphere, 7 g (0.0167 mol) of the product obtained under 6(2), dissolved in 70 ml of dry diethyl ether, are added at ambient temperature to a suspension of 0.38 g (0.01 mol) of AlLiH$_4$ in 30 ml of dry diethyl ether. The mixture is heated for 3 hours at the reflux temperature. It is hydrolysed with 2.6 ml of isopropanol and 3.3 ml of a saturated aqueous solution of NaCl. The mixture is filtered and the material on the filter is rinsed with diethyl ether. The product is extracted into dilute hydrochloric acid and the reaction mixture is then rendered alkaline with NH$_4$OH and extracted with diethyl ether. The ether extract is washed with water, dried over MgSO$_4$, filtered and concentrated. This yields an oil, which is dissolved in 30 ml of ethanol and the solution is added to a filtered solution of 1.2 g (0.0105 mol) of fumaric acid in 60 ml of ethanol. The fumarate precipitates gradually. It is filtered off, rinsed with a small amount of ethanol and then with diethyl ether, and dried. Its melting point is 178°–180° C.

Other compounds of the invention prepared by procedures described in the foregoing Examples are shown in the following Table.

TABLE

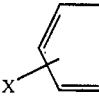
(I)

| Compound | X | R | Salt | Melting point (°C.) of salt |
|---|---|---|---|---|
| 1 | 4-F | H | d,l-mandelate | 146 |
| 2 | 3,4-() | H | d,l,mandelate | 137 |
| 3 | 3,4,5-(OMe)$_3$ | H | d,l-mandelate | 114 |
| 4 | 2-Me | H | d,l-mandelate | 112 |
| 5 | 4-Me | H | d,l-mandelate | 119 |
| 6 | 3-CF$_3$ | H | d,l-mandelate | 126 |
| 7 | 2-OMe | H | hydrochloride | 170 |
| 8 | 3-OMe | H | d,l-mandelate | 117 |
| 9 | 4-OMe | H | d,l-mandelate | 129 |
| 10 | 2-OEt | H | d,l-mandelate | 135 |
| 11 | 3,4-(OMe)$_2$ | H | d,l-mandelate | 108 |
| 12 | H | Me | d,l-mandelate | 118 |
| 13 | H | CO$_2$Et | oil | boiling point (0.4 mm Hg) = 149–151 |
| 14 | 3-CF$_3$ | CH$_2$CH$_2$OH | hydrochloride | 102 |
| 15 | 3,4,5-(OMe)$_3$ | CH(Me)$_2$ | citrate | 94–5 |
| 16 | 3,4,5-(OMe)$_3$ | CO$_2$Et | base | 64 |
| 17 | 3-CF$_3$ | CH(Me)$_2$ | fumarate | 117 |
| 18 | 3-Me | CO$_2$Et | oil | |
| 19 | 3-CF$_3$ | CO$_2$Et | oil | |
| 20 | 3,4,5-(OMe)$_3$ | Me | citrate | |
| 21 | 4-Cl | Me | hydrochloride | 149–151 |
| 22 | 3-CF$_3$ | Me | hydrochloride | 111-2 |
| 23 | 3,4,5-(OMe)$_3$ |  | fumarate | 160–1 |
| 24 | 4-Cl | H | hydrochloride | 157–9 |
| 25 | 3,4-Cl$_2$ | H | hydrochloride | 142.5–144 |
| 26 | 3,4-Cl$_2$ |  | hydrochloride | 184–6 |
| 27 | 3,4-Cl$_2$ | Me | hydrochloride | 119–120 |
| 28 | 4-Cl | CO$_2$Et | oil | |
| 29 | 4-Cl |  | hydrochloride | 171.5–173 |
| 30 | 3,4-Cl$_2$ | CH$_2$CH$_2$OH | hydrochloride | 115.5–117 |
| 31 | 4-O—isoPr | H | fumarate | 140–141.5 |
| 32 | 3,4,5-(OMe)$_3$ |  | fumarate | 178–180 |

TABLE-continued $$\text{X}\underset{}{\overset{}{\diagdown}}\text{—CH}_2\text{—O—}\underset{}{\overset{}{\diagdown}}\text{N—R} \quad (I)$$

| Compound | X | R | Salt | Melting point (°C.) of salt |
|---|---|---|---|---|
| 33 | 4-OMe | CH₂CH₂—C₆H₅ | hydrochloride | 165–7 |
| 34 | 4-isoPr | H | fumarate | 145–6 |
| 35 | 3,4-(—CH=CH—CH=CH—) | H | fumarate | 170–171.5 |
| 36 | 4-OMe | CH₂—C₆H₄—OMe | fumarate | 138–9 |
| 37 | 3,4,5-(OMe)₃ | CH₂—C₆H₄—Cl (2-Cl) | fumarate | 167.5–168.5 |
| 38 | 4-OMe | CH₂—C₆H₄—Cl (4-Cl) | fumarate | 167–8 |
| 39 | 4-OMe | CH₂—C₆H₄—Cl (3-Cl) | fumarate | 152–3 |
| 40 | 4-OMe | CH₂—C₆H₄—Cl (2-Cl) | fumarate | 137–8 |
| 41 | 2,4-Cl₂ | CH₂CH₂OH | fumarate | 106–7 |
| 42 | 3,4,5-(OMe)₃ | CH₂CH₂—C₆H₅ | fumarate | 147–8 |
| 43 | 4-Cl | CH₂CH₂CH₂—C₆H₅ | fumarate | 148–9 |
| 44 | 3,4,5-(OMe)₃ | CH₂—C₆H₄—Cl | fumarate | 180–181.5 |
| 45 | 4-OMe | CH₂CH₂CH₂—C₆H₅ | fumarate | 125.5–127 |
| 46 | 3,4-Cl₂ | CO₂Mo | oil | |
| 47 | 2,4-Cl₂ | CO₂Et | oil | boiling point = 164–8° C./ 0.001 mm |
| 48 | 3,4-(—CH=CH—CH=CH—) | CO₂Et | oil | boiling point = 183–5° C./ 0.003 mm |
| 49 | 4-Br | H | hydrochloride | 205–7 |

The piperidine derivatives of general formula (I) of the present invention were subjected to pharmacological experiments which demonstrated their antidepressive activity.

The toxicity of the compounds was determined on mice by intraperitoneal administration. The LD50 varies from 30 to 1000 mg/kg animal body weight.

The antidepressive activity was determined by the test for the antagonism towards the ptosis caused by reserpine (C. Gouret et al., J. Pharmacol. (Paris) 8, 333–350 (1977)).

Mice (male, CD1 Charles River, France, 18–22 g) simultaneously receive the products to be studied or the solvent (administered intraperitoneally) and reserpine (4 mg/kg animal body weight, administered subcutaneously).

Sixty minutes later, the degree of palpebral ptosis is estimated by means of a rating scale (0 to 4) for each mouse.

For each dose, the average rating and the percentage variation, compared with the control batch, are calculated.

For each product, the AD 50, or the dose which reduces the average ptosis score, compared with the controls, by 50%, is determined graphically.

The AD 50 varies from 4 to 10 mg/kg animal body weight, administered intraperitoneally.

The antidepressive activity was also determined by the test for potentiation of the head twitches caused by L-5-hydroxytryptophan (H. Van Riezen (1972) Arch. Int. Pharmacology, 198, 256–269).

The procedure is as follows.

24 hours before the experiment, the animals are placed in the laboratory in which the operation is to be carried out. On the day of the experiment, the mice are weighed and put to sleep.

The products to be tested are then injected intraperitoneally before L5-HTP is injected subcutaneously in an amount of 125 mg/kg animal body weight as a suspension in Tween. 30 minutes after the injection of L5-HTP, the number of head twitches is counted for 60 seconds.

For each dose, the average number of head twitches and the percentage variation, relative to the control animals, are calculated. The 50% active dose is established from a curve.

The AD 50 varies from 0.1 to 5 mg/kg animal body weight, administered intraperitoneally.

The pharmacological results show that the piperidine derivatives of the present invention can be useful for the treatment of depression.

The compounds of the invention can be presented in any form suitable for oral or parenteral administration, for example in the form of tablets, coated tablets, capsules, solutions to be taken orally or injected, and the like, in association with any suitable excipient.

The daily posology can range from 5 to 200 mg.

We claim:

1. A compound of the formula

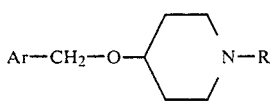

wherein
Ar is naphthyl and
R is a hydrogen atom, $C_1$–$C_4$ alkyl, hydroxy $C_1$–$C_4$ alkyl, $C_1$–$C_4$ alkoxycarbonyl, benzyl, substituted benzyl wherein the substituent is selected from the group consisting of a halogen atom and $C_1$–$C_4$ alkoxy, phenethyl, or 3-phenylpropyl, and a pharmaceutically acceptable acid addition salt thereof.

2. A pharmaceutical composition for treating depression comprising an anti-depressive effective amount of a compound of claim 1 and a pharmaceutically acceptable carrier.

3. A method for treating depression comprising administering to a patient suffering therefrom an anti-depressive effective amount of a compound of claim 1.

* * * * *